United States Patent [19]

Morton, Jr.

[11] 4,403,100

[45] Sep. 6, 1983

[54] (11R)-11-DEOXY-11-ALKYL-6-OXO-PROSTA-GLANDINS

[75] Inventor: Douglas R. Morton, Jr., Kalamazoo County, Mich.

[73] Assignee: The Upjohn Company, Kalamazoo, Mich.

[21] Appl. No.: 316,480

[22] Filed: Oct. 30, 1981

[51] Int. Cl.³ .......................................... C07C 177/00
[52] U.S. Cl. ..................................... 560/121; 560/51; 560/53; 560/108; 560/50; 560/255; 560/231; 560/106; 560/107; 562/503; 562/459; 562/463; 260/408; 260/410; 260/410 S; 260/410.9 R; 260/413; 260/463; 260/464; 260/465 R; 549/78; 549/79; 546/340; 546/342; 568/330; 568/379; 564/453; 564/305; 564/189; 564/169; 424/324; 424/325; 424/305; 424/330; 424/331; 424/317; 424/320

[58] Field of Search .................. 560/121, 51, 53, 108, 560/50, 255, 231, 106, 107; 562/503, 459, 463; 260/410, 410 S, 410.9 R, 413, 408, 463, 464, 465 R; 549/78, 79; 546/340, 342; 568/379, 330; 564/453, 305, 189, 169

[56] References Cited

U.S. PATENT DOCUMENTS 4,124,601 11/1978 Smith ............................ 260/346.22

Primary Examiner—Robert Gerstl
Attorney, Agent, or Firm—Lawrence T. Welch

[57] ABSTRACT

The present invention provides novel (11R)-11-deoxy-11-alkyl-6-oxo-prostaglandins which are useful for curing and preventing duodenal ulcers and for preventing or treating gastrointestinal cell damage caused by the use of other pharmacological agents.

16 Claims, No Drawings

(11R)-11-DEOXY-11-ALKYL-6-OXO-PROSTAGLANDINS

BACKGROUND OF THE INVENTION

The present invention provides novel compositions of matter. This invention further provides novel processes for preparing these compositions of matter. The present invention provides novel (11R)-11-deoxy-11-alkyl-6-oxo-PG type compounds. The 6-oxo-PGE-type compounds from which the compounds of this invention are derived are known in the art and are structural and pharmacological analogs of the prostaglandins.

The prostaglandins are a family of 20 carbon atom fatty acids, being structural derivatives of prostanoic acid, which exhibit useful activity in a wide variety of biological systems. Accordingly, such prostaglandins represent useful pharmacological agents in the treatment and prevention of a wide variety of disease conditions. The term "PG-type compounds" is used to describe structural analogs of the prostaglandins. For a fuller discussion of the prostaglandins, see Bergstrom, et al., Pharmacol. Rev. 20: 1 (1968) and references cited therein.

Similarly, the 6-oxo-PGE type compounds from which the compounds of the present invention are derived exhibit useful activity in a wide variety of biological systems. They also represent useful pharmacological agents in the treatment and prevention of a wide variety of disease conditions.

All of the compounds of the present invention are useful for curing and preventing duodenal ulcers and for preventing or treating gastrointestinal cell damage caused by the use of other pharmacological agents. The compounds of the present invention may also exhibit one or more other useful pharmacological properties. Thus, they may be useful for lowering blood pressure; for inhibiting gastric secretion; for decreasing blood platelet adhesion; for inhibiting blood platelet aggregation and thrombosis formation induced by various physical and chemical stimuli; for the treatment of asthma; for the control of fertility and procreation; and for the treatment of vascular disease states.

PRIOR ART

The known 6-oxo-PGE type compounds are disclosed in U.S. Pat. Nos. 4,215,142; 4,205,178; 4,124,601; 4,251,466; 4,171,447; 4,255,355; 4,246,197; and 4,223,157 and European patent application No. 19069. 6-oxo PGE analogs are also disclosed in copending application No. 070,226. 11-Deoxy-11-alkyl prostaglandins are disclosed in U.S. Pat. Nos. 4,036,871; 4,052,446; 4,187,381; 4,190,587; 4,211,724; and 4,237,060.

SUMMARY OF THE INVENTION

The present invention provides a compound of the formula I, or an enantiomer or a racemic mixture of enantiomers thereof;
wherein $M_1$ is:
 (1) $-(CH_2)_d-C(R_3)_2-$;
 (2) $-CH_2-O-CH_2-Y_1-$;
 (3) cis-$CH_2-CH=CH-$; or
 (4) trans-$CH_2-CH=CH-$;
wherein $N_1$ is
 (1) $-COOR_4$;
 (2) $-CH_2OR_8$;
 (3) $-CH_2NR_5R_6$;
 (4) $-CO-NR_5R_6$;
 (5) $-CN$;
 (6) $-COR_1$; or
 (7) $-COCH_2OH$;
wherein $E_1$ is
 (1) trans-$(CH=CH-$;
 (2) cis-$CH=CH-$;
 (3) $-C\equiv C-$; or
 (4) $-CH_2-CH_2-$;
wherein $Q_1$ is
 (1) $\alpha\text{-}OR_8:\beta\text{-}R_7$;
 (2) $\alpha\text{-}R_{17}:\beta\text{-}OR_8$;
 (3) oxo; or
 (4) $\alpha\text{-}H:\beta\text{-}H$;
wherein $L_1$ is
 (1) $\alpha\text{-}R_9:\beta\text{-}R_{10}$;
 (2) $\alpha\text{-}R_{10}:\beta\text{-}R_9$;
 (3) $\alpha\text{-}OR_8:\beta\text{-}R_7$; or
 (4) $\alpha\text{-}R_7:\beta\text{-}OR_8$;
wherein $R_1$ is $(C_1-C_4)$alkyl;
wherein $R_2$ is
 (1) $-O-(PhX)$;
 (2) $-C_pH_{2p}-(PhX)$;
 (3) $-C_mH_{2m}-(DZ)$;
 (4) $-C_pH_{2p}+1$;
 (5) $-CH_2-CH_2-CH=C(CH_3)_2$;
 (6) $-C_aH_{2a}-O-C_bH_{2b}+1$;
 (7) $-O-(T)$; or
 (8) $-C_pH_{2p}-(Py)$;
wherein (PhX) is phenyl substituted by zero to 3 of the following:
 (1) $(C_1-C_4)$alkyl;
 (2) chloro;
 (3) fluoro;
 (4) bromo;
 (5) nitro;
 (6) trifluoromethyl; or
 (7) $OR_8$;
wherein DZ is a $(C_3-C_6)$ cycloaliphatic substituted by zero to 3 of the following:
 (1) $(C_1-C_4)$alkyl;
 (2) chloro;
 (3) fluoro;
 (4) bromo;
 (5) nitro;
 (6) trifluoromethyl; or
 (7) $OR_8$;
wherein T is 3-thienyl;
wherein Py is 2, 3, or 4-pyridinyl;
wherein $R_3$ is
 (1) hydrogen;
 (2) fluoro; or
 (3) methyl;
wherein $R_4$ is
 (1) hydrogen;
 (2) $(C_1-C_{12})$alkyl;
 (3) $(C_3-C_{10})$cycloalkyl;
 (4) $(C_7-C_{12})$aralkyl;
 (5) phenyl;
 (6) phenyl, mono-, di-, or trisubstituted by chloro or alkyl of from one to 3 carbon atoms, or
 (7) a pharmacologically acceptable cation, or
 (8) phenyl para-substituted by
  (a) $-NHCO-R_{25}$;
  (b) $-O-CO-R_{26}$;
  (c) $-O-CO-R_{24}$;
  (d) $-O-CO-(p\text{-}Ph)-R_{27}$; or
  (e) $-CH=N-NH-CO-NH_2$;

wherein $R_{24}$ is phenyl or acetamidophenyl; $R_{25}$ is methyl, phenyl, acetamidophenyl, benzamidophenyl, or amino, $R_{26}$ is methyl, amino or methoxy; $R_{27}$ is hydrogen or acetamido; and (p-Ph) is 1,4-phenylene; wherein $R_5$ and $R_6$ are the same or different and are
  (1) hydrogen;
  (2) $(C_1-C_4)$alkyl;
  (3) $(C_6-C_{12})$aryl; or
  (4) $(C_7-C_{14})$aralkyl;
wherein $R_7$ is
  (1) hydrogen; or
  (2) $C_1-C_4$ alkyl;
wherein each occurrence of $R_8$ is the same or different and is
  (1) hydrogen;
  (2) $(C_1-C_4)$alkyl; or
  (3) $-COR_{13}$;
wherein $R_9$ and $R_{10}$ are the same or different and are
  (1) hydrogen;
  (2) $(C_1-C_4)$alkyl; or
  (3) fluoro;
wherein $R_{13}$ is
  (1) hydrogen;
  (2) $(C_1-C_{12})$alkyl;
  (3) $(C_3-C_{10})$cycloalkyl;
  (4) $(C_7-C_{12})$aralkyl;
  (5) phenyl; or
  (6) substituted phenyl;
wherein $R_{17}$ is $(C_1-C_4)$alkyl;
wherein $Y_1$ is
  (1) a valence bond; or
  (2) $-(CH_2)_r-$;
wherein d is an integer from 0-5;
wherein p is an integer from 0-8;
wherein m is an integer from 0-3;
wherein q is an integer from 3-6;
wherein a is an integer from 0-2;
wherein b is an integer from 1-5; and
wherein r is an integer from 1-2.

Examples of phenyl esters substituted in the para position (i.e., $N_1$ is $-COOR_4$, $R_4$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester and p-hydroxybenzaldehyde semicarbazone ester.

The carbon atom content of various hydrocarbon-containing moieties is indicated by a prefix designation the minimum and maximum number of carbon atoms in the moiety, i.e., the prefix $(C_i-C_j)$ indicates a moiety of the integer "i" to the integer "j" carbon atoms, inclusive. Thus $(C_1-C_3)$alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of substituted benzyl, phenylethyl, or phenylpropyl are (o-, m-, or p-)tolyl, (o-, m-, or p-)ethylphenyl, 2-ethyl-(o-, m-, or p-)tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-,5- or 6-)chloro-o-tolyl, 4-chloro-2-propylphenyl, 2-isopropyl-4-chlorophenyl, 4-chloro-3,5-xylyl, (2,3-, 2,4-, 2,5-, 2,6- or 3,5-)dichlorophenyl, 4-chloro-3-fluorophenyl, (3- or 4-)chloro-2-fluorophenyl, (o-, m-, or p-)trifluoromethylphenyl, (o-, m-, p-)ethoxyphenyl, (4- or 5-)chloro-2-methoxyphenyl, and 2,4-dichloro-(5- or 6-)methylphenyl.

With regard to the divalent substituents described above (e.g., $L_1$ and $M_1$), these divalent radicals are defined as $\alpha$-$R_i$:$\beta$-$R_j$, wherein $R_i$ represents the substituent of the divalent moiety in the alpha configuration with respect to the plane of the ring and $R_j$ represents the substituent of the divalent moiety in the beta configuration with respect to the plane of the ring. Accordingly, when $M_1$ is defined as $\alpha$-OH:$\beta$-H, the hydroxy of the $M_1$ moiety is in the alpha configuration, and the hydrogen substituent is in the beta configuration.

The prostaglandin analogs of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg to about 500 μg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for the purpose of concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. The compounds of the present invention are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The prostaglandin analog is administered along with the anti-inflammatory prostaglandin synthetase inhibitor either by the same route of administration or by a different route. For example, if the anti-inflammatory substance is being administered orally, the prostaglandin is also administered orally, or alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex, and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experienced the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of prostaglandin to reduce and then substantially to eliminate those undesirable effects.

As an example of the potency of these compounds for the protection of the gastrointestinal tract, in a standard laboratory test (11R)-6-oxo-11-deoxy-11,16,16-trimethyl $PGE_1$ (Example 2 below) exhibits an $ED_{50}$ of 80 μg/kg (when administered orally) in protecting against ethanol induced gastric lesions in the rat.

The compounds of the present invention may also exhibit one or more other useful pharmacological properties as described above. The use of compounds having such utilities are described for example, in U.S. Pat. No. 4,205,178.

As an example of the other useful properties exhibited by one or more of the compounds of this invention, (11R)-6-oxo-11-deoxy-11,16,16-trimethyl $PGE_1$ (Example 2 below) is 100 times as potent as $PGF_{2\alpha}$ in monkey uterine stimulating activity, greater than 32 but less than 100 percent as potent as $PGF_{2\alpha}$ in increasing rat blood pressure in a standard laboratory test, and is an effective antifertility agent in hamsters at between 30 and 1000 μg/animal.

When $N_1$ is $-COOR_4$, the novel compounds are used for the purposes described above in the free acid form, in ester form, and in the pharmacologically acceptable salt form. When the ester form is used, the ester is any of those within the above definition of $R_4$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable cations within the scope of $R_4$ include pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like, aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, glactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

Certain compounds of the present invention are preferred to obtain the optimal combination of biological response, specificity, potency, and duration of activity. Thus, compounds of the formula I, wherein $N_1$ is $-COOH$ or $-COOCH_3$; $M_1$ is $-(CH_2)_2-C(R_3)_2-$ (wherein $R_3$ is hydrogen or fluoro); or trans-$CH_2-CH=CH-$, $R_1$ is methyl; $Q_1$ is $\alpha-OR_8:\beta-R_7$ or $\alpha-R_7:\beta-OR_8$, wherein $R_7$ and $R_8$ are hydrogen or methyl; wherein $L_1$ is $\alpha-R_9:\beta-R_{10}$, $\alpha-R_{10}:\beta-R_9$, $\alpha-OR_8:\beta-R_7$, or $\alpha-R_7:\beta-OR_8$, (wherein $R_7$, $R_8$, $R_9$ and $R_{10}$ are hydrogen or methyl); or $R_2$ is $-O-(PhX)$ wherein PhX is metachlorophenyl), $-(CH_2)_3-CH_3$, $-(CH_2)_4-CH_3-CH_2CH_2-CH=C(CH_3)_2$, $-CH(CH_3)-(CH_2)_3-CH_3$ (S or R), or $(CH_2)_5-CH_3$, are preferred. Compounds which satisfy two or more of these preferences are more preferred and compounds wherein all of the above variables are a preferred substituent are most preferred.

The compounds of the present invention are prepared by the procedures set out in Charts A and B. In the charts, $R_{18}$ is an acid hydrolyzable protecting group or a silyl protecting group of the formula $Si(G_1)_3$. Both of these groups are described more fully below. All other variables are as defined above.

Referring to Chart A, the reactive functional groups of a PGA compound of the formula X, are protected by means well known in the art, as set out below. Thus, all variables containing reactive functional groups (e.g., OH or oxo), are meant to include a protectable group of the Formula $R_{18}$ where appropriate. Conjugate addition of an alkyl group of the formula $R_1$ (wherein $R_1$ is as defined above) to the enone system of formula X is accomplished by the addition of a compound of the formula $(R_1)_2LiCu$ or by a copper mediated Grignard addition.

The ketone function of the compound of the formula XI thus formed is reduced to a hydroxyl group with sodium borohydride or lithium trisec-butylborohydride (L-Selectride ®; Aldrich Chemical Co.), with subsequent chromatographic separation of the C-9 epimers of the formula XII.

The formula XII compound is then converted first to its iodo ether and then to its enol ether by procedures well known in the art. See, e.g., U.S. Pat. No. 4,205,178. The enol ether function of this compound is then hydrolyzed by means well known in the art to the Formula XIII compound.

The hydroxyl function of formula XIII compound thus formed is then oxidized to a ketone by procedures known in the art employing well known oxidation agents set out below. The protecting groups are removed, yielding the final products of formula XIV.

Alternatively, the compounds of the present invention are prepared by the method of Chart B, which is exemplified more fully by the Preparations and Examples set out below.

Referring to Chart B, the hydroxyl function of the lactone of the formula XXI is protected with a protecting group of the formula $R_{18}$, yielding the formula XXII compound. The lactone function is reduced using DIBAL (diisobutylaluminum hydride), by methods well known in the art. See, e.g., U.S. Pat. No. 4,205,178. The formula XXIII compound is converted to the formula XXIV compound by an appropriate Wittig reaction, e.g., reaction with carboxyalkyltriphenylphosphonium bromide. The hydroxyl function is then oxidized to a keto function using well known procedures.

The formula XXV compound thus formed is then depyranylated and then hydrated using the procedures described in U.S. Pat. No. 4,026,909, to yield the formula XXVI compound, which is then converted to the formula XXVII compound by the conjugate addition of $R_1$ as described above. Subsequent reduction of the ketone function, and formation of the iodo ether and enol ether, proceeds as described above for Chart A, ultimately yielding the formula XXIX compound after mild acid hydrolysis. Reductive removal of the benzyl ether group and simultaneous methyl ketal formation is carried out by catalytic hydrogenolysis in methanol in the presence of palladium-on-carbon, to yield the formula XXX compound. Collins oxidation to the corresponding aldehyde, followed by a Wittig-Horner reaction (see, e.g., U.S. Pat. No. 4,016,184), yields the formula XXXI compound. The ketone function is then reduced to the corresponding epimeric alcohols, using, for example, sodium borohydride as described above. The 15-hydroxyl function is protected, and the methyl ketal is hydrolyzed to yield the formula XXXII compound. The conversion of the formula XXXII compound to the final products of formula XXXIII proceeds by well known methods as described above for Chart A and set out more fully below.

$R_{18}$ can be a silyl protecting group of the formula $—Si(G_1)_3$. $G_1$ is alkyl of one to 4 carbon atoms, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, with the proviso that in a $—Si(G_1)_3$ moiety the various $G_1$'s are the same or different and at least one $G_1$ is hindered (such as tert-butyl). Silyl groups within the scope of $—Si(G_1)_3$ include dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, and the like. Examples of aralkyl are benzyl, phenethyl, α-phenylethyl, 3-phenylpropyl, α-naphthylmethyl, and 2-(α-maphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl. Tert-butyldimethylsilyl is most preferred as a silylating agent.

These silyl groups are known in the art. See for example, Pierce "Silylating of Organic Compounds," Pierce Chemical Company, Rockford Ill. (1968). When silylated products of the charts below are intended to be subjected to chromatographic purification, then the use of silyl groups known to be unstable to chromatography is to be avoided. Further, when silyl groups are to be introduced selectively, silylating agents which are readily available and known to be useful in selective silylations are employed. For example, triphenylsilyl and t-butyldimethylsilyl groups are employed when selective introduction is required. A particularly useful silyl group for this purpose is t-butyldimethylsilyl, although other silyl groups are likewise employed.

The acid hydrolyzable protective groups within the scope of $R_{18}$ are any group which replaces a hydroxy hydrogen and is neither attacked by nor is as reactive to the reagents used in the transformations used herein as a hydroxy is and which is subsequently replaceable by acid hydrolysis with hydrogen in the preparation of the prostaglandin-type compounds. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pgs. 51–79 (1969). These blocking groups which have been found useful include:

(a) tetrahydropyranyl;
(b) tetrahydrofuranyl; and
(c) a group of the formula $—C(OR_{11})(R_{12})—CH(R_{13})(R_{14})$, wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $—(CH_2)_a—$ or when $R_{12}$ and $R_{13}$ are taken together $—(CH_2)_b—O—(CH_2)_c$, wherein a is 3, 4, or 5 and b is one, 2 or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group of $R_{18}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the protective group is tetrahydrofuranyl, 2,3-dihydrofuran is used, as described in the preceding paragraph, in place of the 2,3-dihydropyran.

When the protective group is of the formula —C-$(OR_{11})(R_{12})$—CH—$(R_{13})(R_{14})$, wherein $R_{11}$, $R_{12}$, $R_{13}$, and $R_{14}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., Journal of the Chemical Society 86, 3366 (1967). The reaction conditions for such vinyl ethers and unsaturated compounds are similar to those for dihydropyran above.

The protective groups as defined above are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

Suitable oxidation agents to prepare the compounds of this invention include: Jones Reagent (acidified chromic acid, see Journal of American Chemical Society, 39 (1946)), Collins Reagent (chrominium trioxide in pyridine, see Collins, et al., Tetrahedron Lett., 3363 (1968)), mixtures of chromium trioxide in pyridine, see Journal of the American Chemical Society 75, 422 (1953)), tert-butyl chromate in pyridine (see Biological Chemistry Journal, 84 195 (1962)), and mixtures of dicyclohexylcarbodimide and dimethylsulfoxide (see Journal of the American Chemical Society, 87, 5661 (1965)).

For compounds wherein $N_1$ is —COOH, the corresponding ester is converted to its free acid by any of the known methods, e.g., treatment with aqueous potassium hydroxide. Alternatively, the corresponding acid may be obtained by enzymatic hydrolysis using Plexaura homomalla-derived esterase. See, for example W. P. Schneider, et al., J. Am. Chem. Soc. 99:1222 (1977).

DESCRIPTION OF THE PREFERRED EMBODIMENTS

The present invention is more fully understood by the Examples set out below.

PREPARATION 1

5α-Hydroxy-3α-(tetrahydropyran-2-yloxy)-2β-(benzyloxymethyl)-cyclopentyl-1-acetic acid, γ-lactone Refer to Chart B (conversion of Formula XXI to XXII).

A one liter flask, equipped with nitrogen, is charged with 10.7 g (0.04079 moles) of 3α,5α-dihydroxy-2β-(benzyloxymethyl)-cyclopentyl-1-acetic acid, γ-lactone and 250 ml of methylene chloride. The mixture is degassed and flushed twice with nitrogen. To the solution is added 0.4 g of pyridine hydrochloride followed by 35 ml of dihydropyran. The reaction is stirred for 6 hr at room temperature. The reaction mixture is concentrated in vacuo to approximately 75 ml, diluted with brine, and extracted twice with ethyl acetate. The combined organic layers are washed with sodium bicarbonate, brine, and concentrated in vacuo. The crude product is filtered through 500 g of silica gel, packed and eluted with a 1:1 mixture of ethyl acetate-hexane. 40 ml Fractions are collected after an initial 700 ml fraction. Fractions 21–53 are combined to yield 13.0 g of the titled product.

NMR (CDCl$_3$; TMS) peaks are as follows: δ1.23–2.95 (complex m, 12H); 3.25–4.35 (m, 5H); 4.52 (s, 2H); 4.65 (s, 1H); 4.81–5.08 (m, 1H), and 7.35 (s, 5H).

IR (νmax; film) peaks are as follows: 2930, 2850, 1770, 1490, 1460, 1360, 1190, 1170, 1110, 1070, 1020, 970, 910, 870, 790, and 690 cm$^{-1}$.

TLC analysis reveals: Rf=0.37 in 1:1 ethyl acetate-hexane.

PREPARATION 2

5α-Hydroxy-3α-(tetrahydropyran-2-yloxy)-2β-(benzylmethyl)-cyclopentyl-1-acetaldehyde, γ-lactol.

Refer to Chart B (conversion of Formula XXII to XXIII).

A 1-neck one liter flask equipped as in Preparation 1 is charged with 13.0 g (0.0375 moles) of the Formula XXII compound from Preparation 1 and 450 ml of toluene. The mixture is degassed and flushed with nitrogen, cooled to −78° C., and 43 ml of DIBAL (diisobutylaluminum hydride) in toluene is added. The reaction is stirred for 35 min at −78° C. TLC analysis indicates that the reaction is complete. To this reaction is added 200 ml of 1:1 tetrahydrofuran (THF):water. The reaction is warmed to room temperature, diluted with brine, and extracted twice with diethyl ether. The organic phases are washed twice with a 1:1 mixture of 1 normal sodium hydroxide:water, twice with brine, and dried over magnesium sulfate. The mixture is concentrated in vacuo to yield 13.09 g of the titled product is a pale yellow oil.

NMR (CDCl$_3$, TMS) peaks are as follows: δ 1.30–2.50 (complex m, 13H); 3.21–4.28 (m, 5H); 4.35–5.03 (m, 2H); 4.53 (s, 2H); 5.27–5.74 (m, 1H); and 7.40 (s, 5H).

IR (ν max; film) peaks are as follows: 3375 (broad s), 2935, 2850, 1440, 1350, 1190, 1110, 1018, 910, 730, and 690 cm$^{-1}$.

TLC analysis reveals: Rf=0.28 in 1:1 ethyl acetate-hexane.

PREPARATION 3

5α-Hydroxy-3α-(tetrahydropyran-2-yloxy)-2β-(benzyloxymethyl)-1α-[1-(methoxycarbonyl)-cis-4-hexen-6-yl]-cyclopentane Refer to Chart B (conversion of Formula XXIII to XXIV).

A 3-neck 500 ml flask equipped with addition funnel and nitrogen inlet is charged with 6.62 g (0.166 mole) of sodium hydride (which has been rinsed twice with hexane) and 200 ml of dry DMSO (dimethylsulfoxide). The mixture is heated at 65° C. for 1.5 hr, cooled to room temperature, and 36.7 g (0.0828 mole) of 4-carboxybutyltriphenylphosphonium bromide is added dropwise while the mixture is cooling in a water bath. The red mixture is stirred ½ hr at room temperature. A solution of 7.21 g (0.0207 mole) of the Formula XXIII compound from Preparation 2 in 15 ml of tetrahydrofuran (THF) is added dropwise. TLC analysis indicates the reaction is complete after 1 hr. The reaction is allowed to stir a total of 2.5 hr, and is quenched with water, diluted with brine, and extracted with diethyl ether. The organic layer is washed in sodium hydroxide, and all aqueous phases are combined, acidified to pH 3 with cold hydrochloric acid, and extracted twice with ethyl acetate. The organic phases are washed with brine, dried, and concentrated in vacuo to yield crude 5α-hydroxy-3α-(tetrahydropyran-2-yloxy)-2β-(benzyloxymethyl)-1α-(1-carboxy-cis-4-hexen-6-yl)-cyclopentane (Formula XXIV; $N_1$=COOH). This product is chromatographed over 500 g of silica gel eluted with a 40:60 mixture of ethyl acetate:Skellysolve B (SSB). Fractions of 40 ml are collected after an initial 600 ml fraction. Fractions 25-80 yield 9.12 g of the above Formula XXIV ($N_1$=COOH) compound. Spectual analysis of this compound is as follows:

NMR (CDCl$_3$; TMS) peaks are: δ 1.07-2.48 (m, 18H); 3.05-4.33 (m, 8H), 4.51 (s, 2H); 4.57-4.77 (m, 1H); 4.24-5.60 (m, 2H); 7.33 (s, 5H).

IR (ν max; film) peaks are: 3450, 2940, 2840, 1705, 1440, 1330, 1190, 1010, 735, and 675 cm$^{-1}$.

9.12 g (0.0211 moles) of the product of the previous paragraph, 36.8 ml (0.0211 moles) of diisopropylethylamine, and 10.5 ml (0.169 moles) of methyl iodide are added to 300 ml of acetonitrile. The reaction mixture was stirred at 25° C. for 24 hr, diluted with brine and extracted with ethyl acetate. The organic layer was washed with 0.5 M potassium bisulfate-brine (1:1) and dried over magnesium sulfate to yield 8.8 g of the titled product. TLC analysis of this product reveals an Rf of 0.23 in a 35:65 mixture of ethyl acetate:Skellysolve B (a commercial mixture of essentially n-hexane with a boiling point of approximately 60°-68° C.).

PREPARATION 4

5-Oxo-3α-(tetrahydropyran-2-yloxy-2β-(benzyloxymethyl)-1α-[1-(methoxycarbonyl)-cis-4-hexen-6-yl]-cyclopentane Refer to Chart B (conversion of Formula XXIV to XXV).

A 3-necked 500 ml flask equipped with nitrogen inlet is charged with 8.8 g (0.01971 mole) of the Formula XXIV compound from Preparation 3 in 200 ml of dry acetone is degassed and flushed twice with nitrogen, cooled to −25° C. 9.8 ml of 2.67 molar Jones reagent is added dropwise. TLC analysis indicates complete conversion after 45 min at −20° to −30° C. 12 ml of isopropanol are added and the mixture is stirred for approximately 10 min at −25° C., diluted with brine, and extracted three times with diethyl ether. The ether layers are washed with sodium bicarbonate (three times), brine (twice), and dried over magnesium sulfate. The mixture is concentrated in vacuo to yield the crude titled product. This mixture is dissolved in methylene chloride and eluted over 300 g of silica gel using a 35:65 mixture of ethyl acetate:hexane. An initial 340 ml fraction is collected and then 40 ml fractions are collected. Fractions 11-25 yield 7.20 g of the pure titled product.

NMR (CDCl$_3$, TMS) peaks are as follows: δ 1.27-2.50 (m, 18H); 3.26-3.83 (m, 5H); 3.65 (s, 3H); 4.40-4.65 (m, 1H); 4.49 (s, 2H); 5.20-5.43 (m, 2H); and 7.33 (s, 5H).

IR (ν max; film) peaks are as follows: 2930, 2850, 1738, 1458, 1432, 1360, 1317, 1200, 1150, 1075, 1035, 970, 910, 870, 820, 740, and 700 cm$^{-1}$.

TLC analysis reveals: Rf=0.39 in 35:65 ethyl acetate-hexane.

PREPARATION 5

5-Oxo-2β-(benzyloxymethyl)-1α-[1-(methoxycarbonyl)-cis-4-hexen-6-yl]-3-cyclopentene Refer to Chart B (conversion of Formula XXV to XXVI).

A. 5-Oxo-3α-hydroxy-2β-(benzyloxymethyl)-1α-[methoxycarbonyl)-cis-4-hexen-6-yl]-cyclopentane 7.2 g (0.0162 mole) of the Formula XXV compound from Preparation 4 was added to 200 ml of a 20:10:3 solution of acetic acid:water:tetrahydrofuran. The reaction mixture is stirred at 25° C. for 18 hr and at 45° C. for 2 hr, diluted with brine and extracted with ethyl acetate. The organic phase is washed with water twice, sodium bicarbonate twice and brine. The organic phase is then dried over sodium sulfate to yield the crude titled compound. The crude sample is applied to a 300 g silica gel column and eluted with 35:65 solution of ethyl acetate:Skellysolve B. After an initial 340 ml fraction, 40 ml fractions were collected. Fractions 25-70 contained the titled product.

NMR (CDCl$_3$, TMS) peaks are as follows: δ 1.44-2.69 (m, 12H); 3.10 (s, 1H); 3.34-4.40 (m, 3H); 3.63 (s, 3H); 4.55 (s, 2H); 5.22-5.50 (m, 2H); and 7.33 (s, 5H).

IR (ν max; film) peaks are as follows: 3440, 2890, 2860, 1740, 1490, 1450, 1430, 1360, 1310, 1150, 1090, 1070, 1030, 910, 860, 740, and 700 cm$^{-1}$.

TLC analysis reveals: Rf=0.15 in 35:65 ethyl acetate-Skellysolve B.

B. 5-Oxo-2β-(benzyloxymethyl)-1α-[1-(methoxycarbonyl)-cis-4-hexen-6-yl]-3-cyclopentane To a stirred solution of 4.79 g (0.0133 mole) of the product of the previous paragraph in 95 ml of methylene chloride, which has been degassed and flushed with nitrogen and cooled to 0° C. is added 10.7 ml of pyridine followed by 9.3 ml of trifluoroacetic anhydride. The reaction is stirred 20 min at 0° C. 18.5 ml of triethylamine are added dropwise. The reaction is stirred for 20 min at 0° C. Then 18.6 ml of triethylamone are added. The reaction is stirred at 0° C. for 2 hr and at room temperature for ½ hr and at 40° C. for 1 hr. The reaction is diluted with brine and cold 0.5 M potassium bisulfate, and extracted with ether twice. Me ether layers are washed with 0.5 M potassium bisulfate, brine, sodium bicarbonate, brine and dried over magnesium sulfate. The ethereal solution is concentrated in vacuo and the residue is applied to a 400 g silica gel column packed and eluted with a 25:75 mixture of ethyl acetate-Skellysolve B. After an initial 400 ml fraction is collected, 40 ml fractions are collected. Fractions 29-70 contain 5.0 g of the titled product.

NMR (CDCl$_3$, TMS) peaks are as follows: δ 0.96-2.55 (m, 10H); 3.15-3.73 (m, 2H); 3.64 (s, 3H); 4.54 (s, 2H); 5.26-5.54 (m, 2H); 6.20 (dd, J=2 and 6 Hz, 1H); 7.32 (s, 5H); 7.67 (dd, J=2 and 6 Hz, 1H).

IR (ν max; film) peaks are as follows: 2925, 2850, 1725, 1700, 1645, 1590, 1450, 1430, 1350, 1195, 1140, 1010, 870, 740, and 700 cm$^{-1}$.

TLC analysis reveals: Rf=0.38 in 35:65 ethyl acetate-Skellysolve B.

PREPARATION 6

5-Oxo-2β-(benzyloxymethyl)-1α-[1-(methoxycarbonyl)-cis-4-hexen-6-yl]-3α-methyl-cyclopentane Refer to Chart B (conversion of Formula XXVI to XXVII).

To an oven-dried 3-neck 500 ml flask equipped with dropping funnel and nitrogen inlet is charged 4.72 g (0.02476 mole) of cuprous iodide and 200 ml of diethyl ether. The mixture is cooled to 0° C. and 38.1 ml of 1.3 molar methyl lithium in diethyl ether is added dropwise. The reaction turns from a dark yellow to a colorless solution. 4.24 g (0.0124 mole) of the Formula XXVI compound from Preparation 5 in 40 ml of diethylether is added. The reaction is stirred for 15 min at 0° C. and quenched with 13 ml of acetic acid, diluted with brine, and extracted with diethyl ether. The ether layers are washed with saturated sodium carbonate four times, and again with brine. The mixture is dried over magnesium sulfate and concentrated in vacuo. The crude product is applied to 400 g of silica gel and eluted with 20:80 ethyl acetate-Skellysolve B. After an initial 300 ml fraction, 40 ml fractions are collected. The titled product is found in fractions 27–45.

NMR (CDCl$_3$, TMS) peaks are as follows: δ 1.10 (d, 3H); 1.30–2.49 (m, 13H); 3.57 (d, 2H); 3.65 (s, 3H); 4.50 (s, 2H); 5.17–5.42 (m, 2H); 7.33 (s, 5H).

IR (ν max; film) peaks are as follows: 2950, 2850, 1730, 1450, 1430, 1355, 1240, 1200, 1150, 1090, 740, and 700 cm$^{-1}$.

TLC analysis reveals: Rf=0.24 in 25:75 ethyl acetate-Skellysolve B.

PREPARATION 7

5α-Hydroxy-3α-methyl-2β-(benzyloxymethyl)-1α-[methoxycarbonyl)-cis-4-hexen-6-yl]-cyclopentane Refer to Chart B (conversion of Formula XXVII to XXVIII).

An oven-dried 3-necked 100 ml flask equipped with addition funnel and nitrogen inlet is charged with 12.9 ml of L-Selectride ®, and cooled to −78° C. 3.09 g (18.6 mmole) of the Formula XXVII compound from Preparation 7 in 12 ml of tetrahydrofuran is added dropwise. The reaction is stirred 30 min at −78° C. TLC analysis indicates that the reaction is complete. 3.1 ml of 1 N sodium hydroxide and 3.1 ml of 30% hydrogen peroxide are added dropwise while the reaction is maintained at 0° C. The reaction is stirred 15 min at 0°, diluted with water, and extracted with diethyl ether. The ether layers are washed with 1 N sodium hydroxide, and 3 times with brine. The ether phase is dried over magnesium sulfate and concentrated in vacuo. The crude product is applied in methylene chloride to a 400 g silica gel column. The column is eluted with 24% ethyl acetate:74% Skellysolve B: 1% acetic acid. After an initial 450 ml fraction, 40 ml fractions were collected. The product was located in fractions 20–35.

NMR (CDCl$_3$, TMS) peaks are as follows: δ 1.10 (d, 3H); 1.17–2.45 (m, 14H); 3.50 (d, 2H); 3.71 (s, 3H); 4.05–4.27 (m, 1H); 4.57 (s, 2H); 5.16–5.67 (m, 2H); and 7.37 (s, 5H).

IR (ν max; film) peaks are as follows: 3450, 2925, 2850, 1730, 1485, 1455, 1440, 1360, 1317, 1245, 1205, 1100, 1025, 740, and 700 cm$^{-1}$.

TLC analysis reveals: Rf=0.14 in 1:3 ethyl acetate-Skellysolve B.

PREPARATION 8

5α-Hydroxy-3α-methyl-2β-(benzyloxymethyl)-1α-[1-(methoxycarbonyl)-5-oxohex-6-yl]-cyclopentane Refer to Chart B (conversion of Formula XXVIII to XXIX).

A. (1S,5R)-oxa-3ξ-[1-(methoxycarbonyl)-4ξ-iodbut-1-yl]-6β-(benzyloxymethyl)-7α-methyl-bicyclo[3.3.0]octane A 1 liter 1-necked flask equipped with nitrogen inlet was charged with 220 g (6.629 mmole) of the Formula XXVIII compound from Preparation 7. 100 ml of methylene chloride and 1.4 g (13.16 mmole) of sodium bicarbonate are added. The solution is cooled to 0° C. and 1.59 g of iodine is added over 1 min. The mixture is stirred for 50 min at 0° C. and is diluted with 65 ml of 10% sodium sulfite. The organic layer is separated, and the aqueous layers are reextracted with chloroform. The combined organic layers are washed with brine and concentrated in vacuo to yield crude titled product. This product is applied to 150 g of silica gel, packed and eluted with 25:75 ethyl acetate-Skellysolve B. After a 200 ml fraction, 20 ml fractions are collected. Fractions 10–21 contain the titled product.

NMR (CDCl$_3$, TMS) peaks are as follows: δ 1.01 (d, 3H); 1.17–2.68 (m, 14H); 3.22–4.73 (m, 4H); 3.70 (s, 3H); 4.51 (s, 2H); and 7.34 (s, 5H).

IR (ν max; film) peaks are as follows: 2940, 2850, 1730, 1485, 1455, 1365, 1200, 1160, 1100, 730, and 700 cm$^{-1}$.

TLC analysis reveals: Rf=0.22 and 0.24 (isomers at C-5) in 25:75 ethyl acetate-Skellysolve B.

B. 5α-Hydroxy-3α-methyl-2β-(benzyloxymethyl)-1α-[1-(methoxycarbonyl)-5-oxohex-6-yl]-cyclopentane To a solution of 2.45 g (5.037 mmole) of the product of the previous paragraph in 125 ml of toluene is added 5 ml of DBN. The reaction is stirred under nitrogen for 48 hr at room temperature and then heated to 40° C. for 4 hours and at room temperature for 16 hr. The reaction is diluted with brine, extracted with ethyl acetate twice, and the combined extracts are washed with brine, 0.5 molar potassium bisulfate, saturated aqueous sodium bicarbonate, and again with brine. The extract is finally dried over sodium sulfate and concentrated in vacuo to afford a pale green oil. This oil is dissolved in 50 ml of acetone and reacted with 10 ml of water and 1 ml of 1 N hydrochloric acid. After 1.5 hr the reaction mixture is diluted with brine and extracted with ethyl acetate. The extract is washed with brine, dried over magnesium sulfate to give the crude titled product. The product is applied to 150 g of silica gel, packed and eluted with 35:65 ethyl acetate-Skellysolve B. 20 ml Fractions were collected, and fractions 31–63 contain the titled product.

NMR (CDCl$_3$, TMS) peaks are as follows: δ 1.03 (d, 3H); 1.13–2.74 (m, 16H); 3.28–3.52 (m, 2H); 3.64 (s, 3H); 4.27–4.68 (m, 3H); and 7.31 (s, 5H).

TLC analysis reveals: Rf=0.29 in 25:75 ethyl acetate-Skellysolve B.

PREPARATION 9

(1S,5R)-2-Oxa-3ξ-methoxy-3ξ-[1-(methoxycarbonyl)-but-4-yl]-6β-hydroxymethyl-7α-methyl-bicyclo[3.3.0]octane Refer to Chart B (conversion of Formula XXIX to XXX).

A mixture of 0.79 g (2.098 mmole) of the Formula XXIX compound from Preparation 8, 20 ml of methanol, and a total of 300 mg of a 10% palladium on carbon catalyst are hydrogenated for approximately 2 hr. A total of 54.2 ml of hydrogen are absorbed. The calculated uptake is 52 ml. The product is filtered through Celite ® and concentrated in vacuo. The crude residue is diluted with 30 ml of methanol and a catalytic amount of p-toluene sulfonic acid and stirred for 1 hr at room temperature under nitrogen, when triethylamine is added. The mixture is concentrated in vacuo, and applied to a 130 g silica gel column packed and eluted with a 1:1 mixture of ethyl acetate:Skellysolve B containing 1% triethylamine. Fractions 26 to 60 are combined and yield the titled product.

NMR (CDCl$_3$, TMS) peaks are as follows: δ 0.80–2.66 (m, 19H); 3.23 (s, 3H); 3.33–3.82 (m, 2H); 3.73 (s, 3H); and 4.46–4.57 (m, 1H).

TLC analysis reveals: Rf=0.22 and 0.26 (isomers at C-3) in 50:50 ethyl acetate-Skellysolve B.

PREPARATION 10

(11R)-6-Oxo-11-deoxy-11,16,16-trimethyl-15-dehydro-PGF$_1$α, methyl ester, methyl acetal Refer to Chart B (conversion of Formula XXX to XXXI).

A 250 ml 3-necked flask is charged with 30 ml of tetrahydrofuran, cooled to 0° C., and 0.18 g of a 60% oil dispersion of sodium hydride is added. 1.1 g (4.52 mmole) of dimethyl 2-oxo-3,3-dimethylheptylphosphonate in 5 ml of tetrahydrofuran is added. The reaction is stirred for 5 min at 0° C. and 1 hr at room temperature and then cooled to 0° C.

A 250 ml 3-necked flask equipped with nitrogen inlet is charged with 80 ml of methylene chloride and 2.19 ml of pyridine (27.12 mmole) and cooled to 0° C. With vigorous stirring is added 1.36 g of chromium trioxide and the mixture is stirred at room temperature for 30 min. 0.68 g (2.26 mmoles) of the Formula XXX alcohol from Preparation 9 is added in a small amount of methylene chloride. The reaction is stirred at room temperature for 45 min and then cooled to 0° C. The mixture is decanted through a powder funnel with a glass wool plug into the phosphonate anion prepared above. Reaction is stirred at room temperature for 2 hr when an additional 4.52 mmole of phosphonate anion is added to the solution. After 1 additional hr no aldehyde remains. The reaction is poured into a 1:1 brine saturated sodium carbonate solution and extracted with ethyl acetate three times. The organic layers are combined, washed with brine, dried over sodium sulfate, and concentrated in vacuo to afford the crude titled product. The crude product is applied in Skellysolve B to a 130 g silica gel column packed in 15% ethyl acetate:84% Skellysolve B:1% triethylamine. The sample is eluted with 20% ethyl acetate:79% Skellysolve B:1% triethylamine. 20 ml Fractions are collected. The titled product is located in fractions 20–37.

NMR (CDCl$_3$, TMS) peaks are as follows: δ 0.87 (d, 3H); 1.10 (s, 6H); 0.64–2.60 (m, 24H); 3.09 and 3.12 (2s, 3H, isomers at C-6); 3.62 (s, 3H); 4.31–4.64 (m, 1H); and 6.45–6.86 (m, 2H).

IR (ν max; film) peaks are as follows: 2950, 2860, 1735, 1665, 1618, 1460, 1370, 1315, 1240, 1170, 1045 and 985 cm$^{-1}$.

TLC analysis reveals: Rf=0.41 in 25:75 ethyl acetate-Skellysolve B.

PREPARATION 11

(11R,5RS)-6-Oxo-11-deoxy-11,16,16-trimethyl-PGF$_1$α, methyl ester, 15-acetate

Refert to Chart B (conversion of Formula XXI to XXXII).

A. (11R, 15RS)-6-Oxo-11-deoxy-11,16,16-trimethyl-PGF$_1$α, methyl ester, methyl acetal A mixture of 0.8 g (1.89 mmole) of the Formula XXXI compound from Preparation 10 in 15 ml of methanol is cooled to 0° C. 0.14 g (3.69 mmole) of sodium borohydride is added. The solution is stirred for 30 min at −20° C. when TLC analysis reveals no starting material remaining. The reaction is poured into brine, extracted twice with ethyl acetate, and the combined organic layers are washed with brine, dried over magnesium sulfate and concentrated in vacuo to yield 0.8 g of the crude titled product.

NMR (CDCl$_3$, TMS) peaks are as follows: δ 0.51–2.57 (m, 3.4H); 3.17 and 3.20 (2s, 3H, isomers at C-6); 3.70 (s, 3H); 3.67 (m, 1H); 4.27–4.73 (m, 1H); and 5.33–5.61 (m, 2H).

TLC analysis reveals: 0.20, 0.24 and 0.28 (isomers at C-6 and C-15) in 25:75 ethyl acetate-Skellysolve B.

B. (11R, 15RS)-6-Oxo-11-deoxy-11,16,16-trimethyl-PGF$_1$α, methyl ester, 15-acetate Refer to Chart B (conversion of Formula XXI to XXXII).

A mixture of 0.8 g (1.89 mmole) of the product of the previous paragraph, 12 ml of pyridine and 1.2 ml of acetic anhydride are stirred under nitrogen for 1 hr. A catalytic amount of 4-dimethylaminopyridine is added. The reaction is stirred an additional 4 hr when TLC analysis indicates a complete reaction. The reaction is diluted with 0.5 molar potassium bisulfate and extracted twice with ethyl acetate. The combined extracts are washed with 0.5 molar potassium bisulfate, brine, and dried over magnesium sulfate and concentrated in vacuo to afford the C-15 protected methyl acetal 6-methoxy compound. The work-up is completed and the crude product is diluted with 30 ml of a 20:10:3 water:acetic acid:THF solution and stored in a freezer (−20° C.) overnight. The reaction is diluted with brine and extracted with ethyl acetate. The combined organic layers are washed with saturated sodium bicarbonate three times and once with brine, and dried over magnesium sulfate. Finally the mixture is concentrated in vacuo and azeotroped with toluene to remove excessive acetic acid, yielding the titled product.

NMR (CDCl$_3$, TMS) δ 0.53–2.64 (m, 37H); 3.68 (s, 3H); 4.17–4.74 (m, 1H); 4.89–5.10 (m, 1H); and 5.28–5.53 (m, 2H).

EXAMPLE 1

(11R)-6-Oxo-11-deoxy-11,16,16-trimethyl-PGE$_1$, methyl ester, 15-acetate and
(11R,15S)-6-oxo-11-deoxy-11,16,16-trimethyl-PGE$_1$, methyl ester, 15-acetate Refer to Chart B (conversion of Formula XXXII to XXXIII).

To a solution of 0.8 g (1.89 mmole) of the Formula XXXII compound from Preparation 11 in 25 ml of acetone which has been cooled to −25° C. in 100 ml 3-necked flask is added 0.94 ml (2.52 mmole) of Jones reagent. The reaction is stirred for 1 hr at −25° C. when isopropanol (approximately 1.3 ml) is added to quench the reaction. The reaction is stirred for 10 min at −25°

C., diluted with brine, extracted with diethyl ether three times. The ether layers are washed with sodium bicarbonate three times, brine three times, and dried over magnesium sulfate. Finally the mixture is concentrated in vacuo to yield the crude titled products. The crude products were purified by high performance liquid chromatography eluting with 25:75 ethyl acetate-hexane (20 ml fractions). The less polar isomers (Formula XXXIII: $M_1=-(CH_2)_3-$;k $N_1=CO_2CH_3$; $R_1=CH_3$, $E_1=$trans$-CH=CH$; $Q_1=\alpha$-OCOCH$_3$, $\beta$-H; $L_1=CH_3$, CH$_3$; $R_2=-(CH_2)_3CH_3$) was isolated in fractions 63-86 and exhibited NMR absorbances (CDCl$_3$, TMS) at $\delta$ 0.78 and 0.82 (2s, 6H); 1.01 (d, 3H); 1.08-2.62 (m, 24H); 1.98 (s, 3H); 3.59 (s, 3H); 4.88-5.01 (m, 1H); and 5.32-5.48 (m, 2H).

IR ($\nu$ max; film) peaks are as follows: 2955, 2875, 1730, 1450, 1430, 1240, 1165, 1010, 970, and 785 cm$^{-1}$.

TLC analysis reveals: Rf=0.19 in 25:75 ethyl acetate-hexane.

The more polar isomer (Formula XXXIII; $Q_1=\alpha$-H, $\beta$-OCOCH$_3$, is isolated in fractions 87-107 and exhibits NMR absorbances (CDCl$_3$, TMS) at: $\delta$ 0.79 (s, 6H); 1.02 (d, 3H); 1.08-2.64 (m, 24H); 1.98 (s, 3H); 3.40 (s, 3H); 4.87-5.02 (m, 1H); 5.34-5.47 (m, 2H).

IR ($\xi$ max; film) peaks are as follows: 2940, 2875, 1730, 1460, 1430, 1365, 1240, 1165, 1025, and 970 cm$^{-1}$.

TLC analysis reveals: Rf=0.16 in 25:75 ethyl acetate-hexane.

EXAMPLE 2

(11R)-6-Oxo-11-deoxy-11,16,16-trimethyl-PGE$_1$

A solution of 0.36 g of the less polar isomer from Example 1 in 10 ml of 5% potassium hydroxide in 9:1 methanol-water is stirred at room temperature under nitrogen for 4 hr when TLC analysis indicates a complete reaction. The reaction is diluted with brine, acidified to pH 2 with 0.5 M potassium bisulfate, and extracted twice with ethyl acetate. The combined organic layers are washed with brine, concentrated in vacuo to afford the crude titled product. The crude product is applied in methylene chloride to a 10 g acid-washed silica gel column, packed and eluted with 40:60 ethyl acetate-hexane. 20 ml Fractions were collected, and fractions containing the pure titled compound were combined to give 0.298 g.

NMR (CDCl$_3$, TMS) peaks are as follows: $\delta$ 0.77 and 0.83 (2s, 6H); 0.87-2.79 (m, 27H); 3.80 (d, 1H); 4.47 (broad s, 2H); and 5.42-5.62 (m, 2H).

IR ($\nu$ max film) peaks are as follows: 3450, 2950, 2870, 1735, 1470, 1440, 1405, 1370, 1275, 1247, 1095, 1015, and 975 cm$^{-1}$.

TLC analysis reveals: Rf=0.20 in 40% ethyl acetate: 59% Skellysolve B: 1% acetic acid.

Mass spectral analysis reveals the following:

Calcd for C$_{22}$H$_{39}$O$_5$Si: 439.2336. Found: 439.2350 Other ions are observed at m/e 73, 57, 75, 111, 55, 129, 231, 97, 182, and 175.

FORMULA

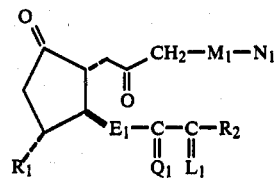

I

CHART A

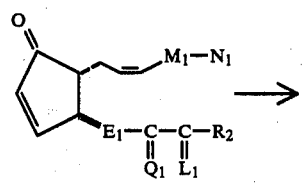

X

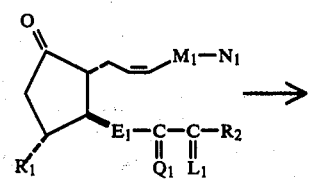

XI

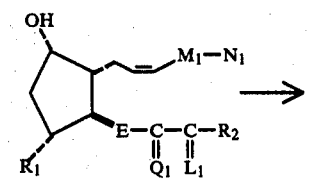

XII

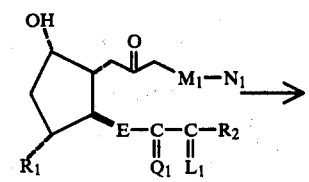

XIII

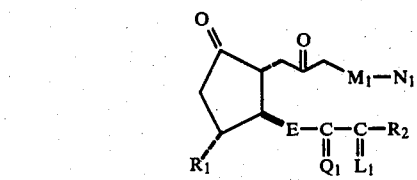

XIV

CHART B

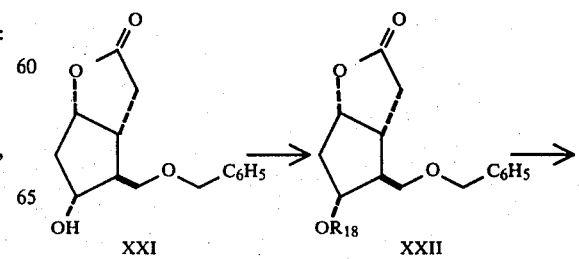

XXI  XXII

-continued
CHART B

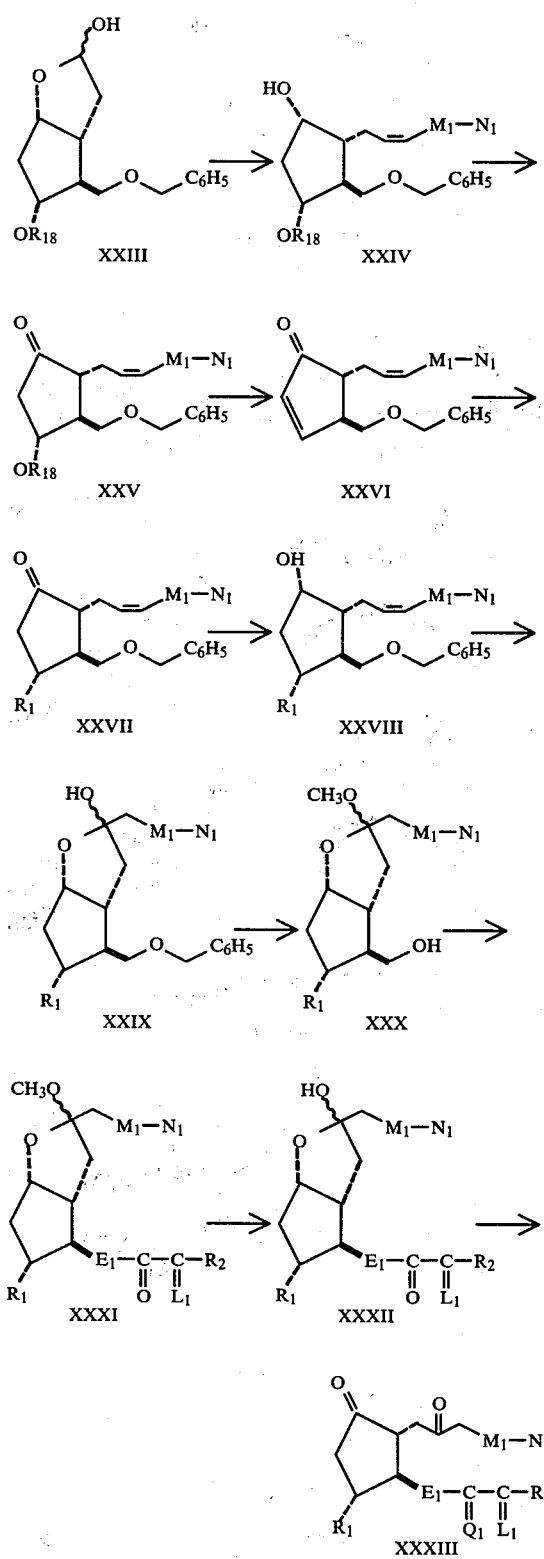

I claim:
1. A compound of the formula I,

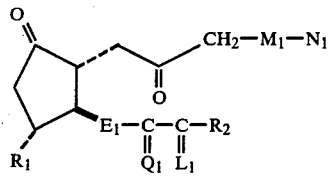

or an enantiomer or a racemic mixture of enantiomers thereof;
wherein $M_1$ is:
(1) $-(CH_2)_d-C(R_3)_2-$;
(2) $-CH_2-O-CH_2-Y_1-$;
(3) cis-$CH_2-CH=CH-$; or
(4) trans-$CH_2-CH=CH-$;
wherein $N_1$ is
(1) $-COOR_4$;
(2) $-CH_2OR_8$;
(3) $-CH_2NR_5R_6$;
(4) $-CO-NR_5R_6$;
(5) $-CN$;
(6) $-COR_1$; or
(7) $-COCH_2OH$;
wherein $E_1$ is
(1) trans-$CH=CH-$;
(2) cis-$CH=CH-$;
(3) $-C\equiv C-$; or
(4) $-CH_2-CH_2-$;
wherein $Q_1$ is
(1) $\alpha\text{-}OR_8{:}\beta\text{-}R_7$;
(2) $\alpha\text{-}R_{17}{:}\beta\text{-}OR_8$;
(3) oxo; or
(4) $\alpha\text{-}H{:}\beta\text{-}H$;
wherein $L_1$ is
(1) $\alpha\text{-}R_9{:}\beta\text{-}R_{10}$; or
(2) $\alpha\text{-}R_{10}{:}\beta\text{-}R_9$;
wherein $R_1$ is $(C_1-C_4)$alkyl;
wherein $R_2$ is
(1) $-O-(PhX)$;
(2) $-C_pH_{2p}-(PhX)$;
(3) $-C_mH_{2m}-(DZ)$;
(4) $-C_pH_{2p}+1$;
(5) $-CH_2-CH_2-CH=C(CH_3)_2$;
(6) $-C_aH_{2a}-O-C_bH_{2b}+1$;
(7) $-O-(T)$; or
(8) $-C_pH_{2p}-(Py)$;
wherein (PhX) is phenyl substituted by zero to 3 of the following:
(1) $(C_1-C_4)$alkyl;
(2) chloro;
(3) fluoro;
(4) bromo;
(5) nitro;
(6) trifluoromethyl; or
(7) $OR_8$;
wherein DZ is a $(C_3-C_6)$ cycloaliphatic substituted by zero to 3 of the following:
(1) $(C_1-C_4)$alkyl;
(2) chloro;
(3) fluoro;
(4) bromo;
(5) nitro;
(6) trifluoromethyl; or
(7) $OR_8$;
wherein T is 3-thienyl;
wherein Py is 2, 3, or 4-pyridinyl;
wherein $R_3$ is (1) hydrogen;
(2) fluoro; or
(3) methyl;
wherein $R_4$ is
(1) hydrogen;
(2) $(C_1-C_{12})$alkyl;
(3) $(C_3-C_{10})$cycloalkyl;
(4) $(C_7-C_{12})$aralkyl;
(5) phenyl;
(6) phenyl, mono-, di-, or trisubstituted by chloro or alkyl of from one to 3 carbon atoms; or
(7) a pharmacologically acceptable cation, or
(8) phenyl para-substituted by
  (a) —NHCO—$R_{25}$;
  (b) —O—CO—$R_{26}$;
  (c) —O—CO—$R_{24}$;
  (d) —O—CO—(p-Ph)—$R_{27}$; or
  (e) —CH=N—NH—CO—$NH_2$;
wherein $R_{24}$ is phenyl or acetamidophenyl; $R_{25}$ is methyl, phenyl, acetamidophenyl, benzamidophenyl, or amino, $R_{26}$ is methyl, amino or methoxy; $R_{27}$ is hydrogen or acetamido; and (p-Ph) is 1,4-phenylene, wherein $R_5$ and $R_6$ are the same or different and are
(1) hydrogen;
(2) $(C_1-C_4)$alkyl;
(3) $(C_6-C_{12})$aryl; or
(4) $(C_7-C_{14})$aralkyl;
wherein $R_7$ is
(1) hydrogen; or
(2) $C_1-C_4$ alkyl;
wherein each occurrence of $R_8$ is the same or different and is
(1) hydrogen;
(2) $(C_1-C_4)$alkyl; or
(3) —$COR_{13}$;
wherein $R_9$ and $R_{10}$ are the same or different and are
(1) hydrogen;
(2) $(C_1-C_4)$alkyl; or
(3) fluoro;
wherein $R_{13}$ is
(1) hydrogen;
(2) $(C_1-C_{12})$alkyl;
(3) $(C_3-C_{10})$cycloalkyl;
(4) $(C_7-C_{12})$aralkyl;
(5) phenyl; or
(6) substituted phenyl;
wherein $R_{17}$ is $(C_1-C_4)$alkyl;
wherein $Y_1$ is
(1) a valence bond; or
(2) —$(CH_2)_r$—;
wherein d is an integer from 0-5;
wherein p is an integer from 0-8;
wherein m is an integer from 0-3;
wherein q is an integer from 3-6;
wherein a is an integer from 0-2;
wherein b is an integer from 1-5; and
wherein r is an integer from 1-2.

2. A compound of claim 1 wherein $N_1$ is —COOH or —$COOCH_3$; $M_1$ is —$(CH_2)_2$—$C(R_3)_2$— or trans-$CH_2$—$CH$=$CH$—, wherein $R_3$ is hydrogen or fluoro; $R_1$ is methyl; $Q_1$ is $\alpha$-$OR_8$:$\beta$-$R_7$ or $\alpha$-$R_7$:$\beta$-$OR_8$, wherein $R_7$ and $R_8$ are hydrogen or methyl; wherein $L_1$ is $\alpha$-$R_9$:$\beta$-$R_{10}$, or $\alpha$-$R_{10}$:$\beta$-$R_9$, wherein $R_7$, $R_8$, $R_9$ and $R_{10}$ are hydrogen or methyl; and $R_2$ is —O—(PhX), wherein PhX is metachlorophenyl, —$(CH_2)_3$—$CH_3$, —$(CH_2)_4$—$CH_3$, —$CH_2$—$CH_2$—$CH$=$C(CH_3)_2$, —$CH(CH_3)$—$(CH_2)_3$—$CH_3$ (S or R), or $(CH_2)_5$—$CH_3$.

3. (11R)-6-Oxo-11-deoxy-11,16,16-trimethyl-$PGE_1$, methyl ester, 15-acetate, a compound of claim 1.

4. (11R)-6-Oxo-11-deoxy-11,16,16-trimethyl-$PGE_1$, a compound of claim 2.

5. (11R)-6-Oxo-11-deoxy-11,16($\xi$)-dimethyl-$PGE_1$, a compound of claim 2.

6. (11R)-6-Oxo-11-deoxy-11,15-dimethyl-$PGE_1$, a compound of claim 2.

7. (11R)-6-Oxo-11-deoxy-11,16($\xi$)-dimethyl-16($\xi$)-hydroxy-$PGE_1$, a compound of claim 2.

8. (11R)-6-Oxo-11-deoxy-11,16,16-trimethyl-20-isopropylidene-$PGE_1$, a compound of claim 2.

9. (11R)-6-Oxo-11-deoxy-11,17(S),20-trimethyl-2,2-difluoro-6-keto-$PGE_1$, methyl ester, a compound of claim 2.

10. (11R)-6-Oxo-11-deoxy-11,17(S),20-trimethyl-$PGE_1$, methyl ester, a compound of claim 2.

11. (11R)-6-Oxo-11-deoxy-11,16,16-trimethyl-2,2-difluoro-$PGE_1$, methyl ester, a compound of claim 2.

12. (11R)-6-Oxo-11-deoxy-11,17(S),20-trimethyl-trans-2,3-didehydro-$PGE_1$, a compound of claim 2.

13. (11R)-6-Oxo-11-deoxy-11,16,16-trimethyl-trans-2,3-didehydro-$PGE_1$, methyl ester, a compound of claim 2.

14. (11R)-6-Oxo-11-deoxy-11,20-dimethyl-$PGE_1$, methyl ester a compound of claim 2.

15. (11R)-6-Oxo-11-deoxy-11-methyl-20-ethyl-$PGE_1$, methyl ester a compound of claim 2.

16. (11R)-6-Oxo-11-deoxy-11-methyl-16-(m-chlorophenoxy)-17,18,19,20-tetranor-$PGE_1$, a compound of claim 2.

* * * * *

UNITED STATES PATENT OFFICE
CERTIFICATE OF CORRECTION

Patent No. 4,403,100      Dated 6 September 1983

Inventor(s) Douglas R. Morton, Jr.

It is certified that error appears in the above-identified patent and that said Letters Patent are hereby corrected as shown below:

Column 2, line 6, "trans-(CH=CH-;" should read -- trans-CH=CH-; --.
Column 6, line 61, "...-$CH_3$-$CH_2CH_2$-..." should read -- ...-$CH_3$-$CH_2$-$CH_2$- ... --.
Column 7, line 49, "then hydrated" should read -- then dehydrated --.
Column 19, line 53, (Formula XXXII), "$E_1$-C—C-$R_2$" should read -- $E_1$-C—C-$R_2$ --
$$E_1-\underset{\underset{O}{\|}}{C}-\underset{\underset{L_1}{\|}}{C}-R_2 \quad\quad E_1-\underset{\underset{Q_1}{\|}}{C}-\underset{\underset{L_1}{\|}}{C}-R_2$$

Signed and Sealed this

Fifteenth Day of May 1984

[SEAL]

*Attest:*

*Attesting Officer*

GERALD J. MOSSINGHOFF

*Commissioner of Patents and Trademarks*